United States Patent [19]

Puzig

[11] Patent Number: 4,677,130
[45] Date of Patent: Jun. 30, 1987

[54] PROCESS OF DENSIFICATION OF N-HALOHYDANTOIN COMPOSITIONS AND PRODUCTS THEREOF

[75] Inventor: Edward H. Puzig, West Lafayette, Ind.

[73] Assignee: Great Lakes Chemical Corporation, West Lafayette, Ind.

[21] Appl. No.: 785,210

[22] Filed: Oct. 7, 1985

[51] Int. Cl.$^4$ .................. C07D 403/30; A61K 33/22; A61K 31/41; A01N 59/14
[52] U.S. Cl. .................................. 514/389; 514/390; 514/960; 548/311; 424/148; 424/155; 424/156
[58] Field of Search .................. 514/960, 389, 390; 548/311; 424/148, 155, 156

[56] References Cited

U.S. PATENT DOCUMENTS

| | | | |
|---|---|---|---|
| 2,430,233 | 11/1947 | Magill | 548/311 |
| 2,779,764 | 1/1957 | Paterson | 548/311 |
| 2,868,787 | 1/1959 | Paterson | 544/215 |
| 2,986,555 | 5/1961 | Paterson | 525/329.3 |
| 3,147,219 | 9/1964 | Paterson | 514/150 |
| 3,345,371 | 8/1965 | Paterson | 534/588 |
| 3,412,021 | 11/1968 | Paterson | 514/245 |
| 3,639,168 | 2/1972 | Monti et al. | 424/156 |
| 4,203,997 | 5/1980 | Küppers et al. | 514/960 |
| 4,427,692 | 1/1984 | Girard | 514/390 |
| 4,517,179 | 5/1985 | Raghunathan | 514/960 |
| 4,532,330 | 7/1985 | Cole | 548/311 |
| 4,560,766 | 12/1985 | Girard et al. | 548/311 |

OTHER PUBLICATIONS

Chem. Abstr. 101:28296f (Levy et al.).
Chem. Abstr. 100:39099x (Kibbel).
Chem. Abstr. 99:89920q (Dirkse).
Chem. Abstr. 98:37049x (Sumitomo).
Chem. Abstr. 97:184817d (Japan Carlit).
Chem. Abstr. 96:70819e (Lichtenberg).
Chem. Abstr. 86:142347t (Novy).
Chem. Abstr. 78, 65192u.

Primary Examiner—Ronald W. Griffin
Attorney, Agent, or Firm—Senniger, Powers, Leavitt and Roedel

[57] ABSTRACT

The present invention is directed to a novel process for manufacturing tablets of N-halohydantoin compounds. In the process, at least one dry, particulate N-halohydantoin compound is blended with a dry, particulate alkali metal or alkaline earth salt to form a dry mixture, and the mixture is compacted into densified forms such as tablets. Dry particulate alkali metal or alkaline earth salts consist of a cation selected from among the group comprising lithium, sodium, potassium, magnesium and calcium and an anion selected from among the group comprising carbonate, bicarbonate, borate, silicate, phosphate, percarbonate, and perphosphate, to form a dry mixture and compressing the mixture.

The invention is further directed to tablets produced by this process. The invention is also directed to mixtures comprising N-halohydantoin, one-half to three percent by weight alkali metal or alkaline earth salt, minor components and less than about five percent water. The invention is still further directed to densified mixtures consisting essentially of N-halohydantoin, one-half to three percent by weight alkali metal or alkaline earth salt, and less than about five percent water.

25 Claims, No Drawings

PROCESS OF DENSIFICATION OF N-HALOHYDANTOIN COMPOSITIONS AND PRODUCTS THEREOF

BACKGROUND OF THE INVENTION

This invention relates to product forms of N-halohydantoin compounds, and more particularly to densification of N-halohydantoin forms. Still more particularly, this invention relates to the densification of dry N,N'-dihalohydantoin particulate solids mixed with chemical additives into tablets that withstand the stresses of automatic packaging, conveying handling, shipping, storage and use equipment.

N-halohydantoin compounds are highly efficient halogen donors for effecting various organic syntheses. In water, such compounds provide a low concentration of active halogen and are thus useful as bacteriocides in water treatment processes. Particularly effective halogen sources are N,N'-dihalohydantoin compounds such as 1-bromo-3-chloro-5,5-dimethylhydantoin, 3-bromo-1-chloro-5,5-dimethylhydamtoin, 1,3-dibromo-5,5-dimethylhydantoin and 1,3-dichloro-5,5-dimethylhydantoin.

N-halohydantoin compounds are ordinarily produced as particulate solids. However, for certain uses, it is desired to compact, agglomerate, extrude or otherwise densify particulate N,N'-dihalohydantoin compounds into forms such as tablets or briquettes. For such purposes, it is necessary to utilize a formulation which, when formed under mechanical pressure into a predetermined shape, is strong enough to withstand the shocks, stresses and pressures resulting from automated packaging, conveying, handling, shipping, storage and use equipment. Conventionally, it is necessary for tablets formed from particulate N,N'-dihalohydantoin compounds to be oven dried or "cured" to possess sufficient strength or "hardness" to withstand subsequent handling and packaging operations. Oven-drying is undesirable, however, because it requires an extra processing step, uses energy and requires further delays for cooling.

Other problems exist in the conventional methods of compressing N-halohydantoin compounds. The essentially unavoidable presence of some water, even at concentrations of only one-half to five percent, results in corrosion of the compaction equipment by the acidity produced by hydrolysis of the N-halohydantoin in the tablet. Another disadvantage of the conventional methods is that the acidity produced by hydrolysis of N,N'-dihalohydantoin compounds within the densified products reduces alkalinity in treated waters.

Various chemical additives have been introduced to N,N'-dihalohydantoin for various purposes. U.S. Pat. No. 3,412,021 (Paterson) discloses a method (and product formed thereby) involving the mixing of 1-bromo-3-chloro-5,5-dimethylhydantoin with various additives in the presence of copious water. In column 4, lines 67–69, it is noted that polymers added as binders are added as solutions, including aqueous solutions. These binders are added to enable the forming of sticks or rods and to reduce the disintegration rate of N,N'-dihalohydantoin in water. Further, in each example in the patent, sufficient water is added to form a paste consisting of at least 25% water.

Since excessive water in the product will render the chemical additive inactive pertaining to its curing properties, the method of Paterson does not yield acceptable tablets of N-halohydantoin compounds. Nor does the method of Paterson produce such tablets of increased hardness unless subjected to oven drying.

Paterson also does not disclose compressing or densifying the mixture. The method of Paterson consists of wet-forming (again, copious water is required) the halogenated compound by molding or extrusion. The method disclosed in Paterson improves the strength of the particulate so as to enable the mixture to be formed into sticks. After the mixture is extruded and dried, interstices previously occupied by water constitute voids within the crystalline structure. While the binders added in Paterson allow the formation of rods, the density of the mixture is actually decreased. The rods are therefore fragile and do not withstand stresses from the packaging equipment. Tablets cannot be formed by compression when the water content approaches that suggested by Paterson. At such water concentrations, excess alkalinity in the chemical additive reacts with acidity produced by hydrolysis of N-halohydantoin compounds, causing the chemical additive to become inactive and hardening is not achieved. Therefore, even upon the advent of Paterson, there was still a need for a method to create densified N-halohydantoin which can withstand the stresses of the automated handling equipment.

Moreover, many disadvantages have arisen from the use of chemical additives. For example, the chemical additives may react with the N,N'-halohydantoin compound or otherwise interfere with the desired uses of the N,N'-halohydantoin compounds, such as by reducing the dissolution rates of the compounds.

SUMMARY OF THE INVENTION

Among the several objects of the present invention, therefore, may be noted the provision of a process for the manufacture of hardened, densified N-halohydantoin compositions without the need for oven drying. Another object of this invention is the provision of dry N-halohydantoin compositions densified into tablets which can withstand automated packaging, conveying and handling, and which are free of additives that react or otherwise interfere with the desired uses of the densified N,N'-halohydantoin compounds, such as by reducing the dissolution rates of the compounds.

Still another object is to reduce the corrosion of compaction equipment caused by free acids in dry densified N-halohydantoin compounds. Yet another object is to eliminate the reduction of alkalinity in treated waters caused by the acidity of dry N-halohydantoin compounds within the densified products.

Briefly, therefore, the present invention is directed to a novel process for manufacturing tablets of N-halohydantoin compounds of the formula

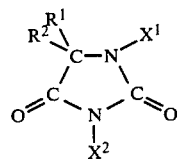

where $R^1$ and $R^2$ are independently selected from among hydrogen and low molecular weight alkyl groups, and $X^1$ and $X^2$ are independently selected from among bromine, chlorine and hydrogen, at least one of $X^1$ and $X^2$ being halogen. In the process, at least one dry, particulate N-halohydantoin compound is blended with a dry, particulate alkali metal or alkaline earth salt to form a dry mixture, and the mixture is compacted into densified forms, such as tablets. Dry particulate alkali metal or alkaline earth salts consist of a cation selected from among the group comprising lithium, sodium, potassium, calcium, and magnesium and a anion selected from among the group comprising carbonate, bicarbonate, borate, silicate, phosphate, percarbonate, and perphosphate, to form a dry mixture by compressing the mixture.

The invention is further directed to tablets produced by this process. The invention is also directed to mixtures comprising N-halohydantoin, one-half to three percent by weight alkali metal or alkaline earth salt, minor components and less than about five percent water. The invention is still further directed to densified mixtures consisting essentially of N-halohydantoin, one-half to three percent by weight alkali metal or alkaline earth salt, and less than about five percent water.

Other objects and features of this invention will be in part apparent and in part pointed out hereinafter.

DESCRIPTION OF PREFERRED EMBODIMENTS

In accordance with this invention, a process has been discovered by which densified N-halohydantoin compositions can be formed having sufficient hardness to withstand automated packaging and handling operations without the need for oven-drying. By mixing at least one dry, particulate N-halohydantoin compound with a dry, particulate alkali metal or alkaline earth salt and mechanically compressing the mixture, tablets or other densified forms are created that are even harder than the oven-dried tablets previously known to the art. The entire process can be carried out under dry conditions, and it is essential that the mixture be dry during the compression step. As used in the context of this disclosure, "dry" means that the water concentration does not exceed about five percent.

It has been found that the alkali metal and alkaline earth salts do not undesirably react with the N-halohydantoin compounds or otherwise interfere with the desired uses of the compounds. It has also been found that the additive compounds contemplated by this invention reduce the corrosion of the compaction machinery ordinarily caused in the tableting process. Although not wishing to be bound to one particular theory, it is believed that the basic ion of the additive salts neutralizes any acid produced by water present, even in the low 0.5% to 5.0% range of concentration, in the compaction process. This also is believed to explain how reduction in alkalinity of the treated water is avoided by use of tablets of the present invention.

Another of the benefits of this invention is the capability of avoiding of the previously essential oven drying step. By avoiding this step, energy is saved as are the extra time for the oven drying and the costs entailed by the extra curing step.

This invention concerns the densification of N-halohydantoin compounds of the formula

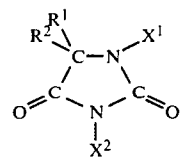

where $R^1$ and $R^2$ are independently selected from among hydrogen and lower alkyl groups and $X^1$ and $X^2$ are independently selected from among bromine, chlorine and hydrogen, at least one of $X^1$ and $X^2$ being halogen. While in the examples below, $R^1$ and $R^2$ are each methyl, they can also comprise other lower alkyls of up to nine carbon atoms, for example ethyl, n-propyl, iso-propyl, n-butyl or n-pentyl, to form, for example, N,N'-halogenated-5,5-dimethylhydantoin, N,N'-halogenated-5,5-methylethylhydantoin, and N,N'-halogenated-5,5-diethylhydantoin. Particularly preferred bacteriocides include 1,3-dibromo-5,5-dimethylhydantoin, 1-bromo-3-chloro-5,5-dimethylhydantoin, 3-bromo-1-chloro-5,5-dimethylhydantoin, 1-3-dichloro-5,5-dimethylhydantoin, 1- or 3-bromo-5,5-dimethylhydantoin, 1- or 3-chloro-5,5-dimethylhydantoin, or a N-halohydantoin compositions containing any combination of these compounds in any proportion.

Dry particulate alkali metal or alkaline earth salts consist of a cation selected from among the group comprising lithium, sodium, potassium, magnesium and calcium and an anion selected from among the group comprising carbonate, bicarbonate, borate, silicate, phosphate, percarbonate, and perphosphate. Calcium containing additive compounds have been found to not be as advantageous since the calcium in the presence of chlorine from BCDMH tends to form hygroscopic calcium chloride.

So as to avoid undesirable reactions, the alkali metal and alkaline earth salts must not be highly acidic or highly basic. If highly basic, the salt will disadvantageously react with the halohydantoin compound. If highly acidic, the salt will not achieve the above described advantages of reducing corrosion and eliminating reduction in alkalinity. While the salt may be slightly acidic or slightly alkaline like sodium carbonate, it is preferred that the salt be neutral to slightly alkaline to avoid corrosion and reduction of alkalinity. The problem of the additive reacting with the N-halohydantoin compound does not arise unless the additive is relatively highly alkakline. Preferably, the pH of a 0.1% solution prepared from 1-bromo-3-chloro-5,5-dimethylhydantoin (BCDMH) and salt ranges from about 6.5 to about 7.5.

It has further been discovered that optimum results in the production of cured or hardened tablets are obtained when the size of the compacted particulate solids is substantially within the sieve classification range of $-10$ to $+20$, the water content of the particulate solids is between 0.5% and 5.0% by weight, the tablets contain up to about three percent by weight salt additive, and the tablets are aged or cured for at least twenty-four to forty-eight hours. By "substantially within the sieve classification range of $-10$ to $+20$" what is meant is at most about ten percent by weight of the particles are outside that range. The tablets, or other densified form of the mixture also contain minor components, such as sodium stearate in concentrations on the order of about 0.1% by weight and trace amounts of sodium chloride.

Sodium stearate is used as a die lubricant. Sodium chloride is a natural by-product of the manufacturing process. The tablets have a density of about 1.5 grams per cubic centimeter to about 1.8 grams per cubic centimeter. In contrast, the rods produced by the method of Paterson have a density of only about 1.2 grams per cubic centimeter. Therefore the rods produced by the method of Paterson are considerably more fragile than the tablets produced by the method disclosed herein.

Tablets with additives are formed by blending dry, particulate additive with a dry, particulate N-halohydantoin composition to form a mixture and transferring the mixture to a tableting machine such as a Stokes rotary press. Conventional blending equipment is used, a twin shell or Vee mixer being particularly suitable. The amount of the additive blended with the N-halohydantoin compound is determined by the concentrations desired in the final product. The N-halohydantoin compounds, themselves, may be produced by a process similar to that described in Example 1, below.

It has been found that presence in the mixture of one-half to three percent by weight additive is sufficient to produce a hardened tablet. While additives have been tested in the examples below in concentrations of one to three percent, it is anticipated that certain additives, particularly sodium silicate, in lower concentrations, probably at least as low 0.5%, will impart adequate hardness to N-halohydantoin tablets. The upper limit of additive concentration is generally constrained only by the desired assay of the final product.

It has also been found that aging the additive containing tablets at ambient temperatures for twenty-four to forty-eight hours increases the hardness of the tablets even further. Such aging requires no extra step in practice since aging ordinarily occurs as a natural effect in the normal tablet handling operations. Where tablets were aged or cured by aging in the examples below, such aging was accomplished merely by placing tablets in buckets, covering each bucket with a lid and storing the tablets in the buckets at ambient temperature for the indicated period of time, similar to the normal procedures followed in the manufacture and subsequent distribution of tablets.

Surprisingly, the addition of alkali metal or alkaline earth salts to N-halohydantoin compounds allows production of tablets that are even harder than oven-dried tablets produced without the additives. Another surprising advantage of this invention is that while the additives increase the hardness of the tablets, they do not appreciably affect, neither increasing nor decreasing, the dissolution rates of N-halohydantoin compounds.

It has further been found that while water concentrations approaching two percent may improve the hardness of tablets, the tablets are more stable at lower water concentrations. Tablets containing two percent water tend to discolor with time. As a result, it has been found that water concentrations of less than 1.5 percent are optimal. It should also be noted that although certain water concentrations have been found to affect the hardness of N-halohydantoin tablets, it is not commercially feasible to vary hardness by controlling water content. In a commercial process it is very difficult to control and maintain the water content.

Whereas the compounds of this invention may be densified in a number of ways, such as by compressing, extruding and agglomerating, the term "compacting" will be used to indicate any of them.

The following examples illustrate the invention.

EXAMPLE 1

1-Bromo-3-chloro-5,5-dimethylhydantoin (BCDMH) was produced by initially charging water (7500 pounds), followed by dimethylhydantoin (1700 pounds), to a 2000 gallon reactor. Next, bromine (1061 pounds) and a 20% aqueous solution of sodium hydroxide (1327 pounds), and then chlorine (1413 pounds) and a 20% aqueous solution of sodium hydroxide (3986 pounds) were added at a rate such that the solution did not exceed a temperature of twenty-five degrees Celsius, while the pH of the solution was controlled at 6.8 to 7.0. The resulting slurry was filtered and washed with water, producing a filtered cake which was then extruded and dried into stick form. Ground sticks were compacted in a granulator and sieved, producing dry particulate BCDMH. Tablets without additives were made by transfering dry, particulate BCDMH to a Stokes rotary press tableting machine. Tablets with additives were made by blending dry, particulate additive with dry, particulate BCDMH and transfering the mixture to a Stokes rotary tableting machine.

EXAMPLE 2

Standard sieve analysis was conducted involving passing BCDMH through a sieve. The particles were separated into the sizes listed below. Tablets of the various size particles were formed as described in Example 1. Tests comparing the size of the particles of solid to the hardness or average green (unaged tablet) crush strength as measured in pounds per square inch for tablets of 99.9% BCDMH and tablets containing three percent additve (sodium carbonate) were performed as follows. A tablet was placed on edge on the platform of a Rimac spring strength tester. A handle which drives a piston was moved downwardly with pressure as measured on a spring driving gauge. Pressure was increased until the tablet broke. The pressure at the point of breakage was measured in pounds per square inch ("psi"). The tests yielded the following results:

| | Average Green Crush Strength psi at Break | |
|---|---|---|
| Sieve Classification | 99.9% BCDMH | 3% Na2CO3 |
| −8 to +10 | 26.0 | 24.0 |
| −10 to +20 | 43.2 | 60.8 |
| −20 to +40 | 55.2 | 54.8 |

The sieve size selected as best for the tablet manufacturing process, −10 to +20, produces the hardest tablets upon curing because of minimal separation of BCDMH particulate solids and chemical additive upon blending. These results are reproducible when providing the same size sodium carbonate particulate. BCDMH particulate solids classified in the range −20 to +40 provides for the manufacture of tablets with acceptable hardness without chemical additives. However, this sieve size represents only a small portion of the granulated product and would reduce tablet production with existing equipment. Other disadvantages of using a smaller sieve sized BCDMH particulate for the tableting process without chemical additives are that it would increase down time, maintenance and corrosion of the tableting press.

EXAMPLE 3

Tablets of various water contents were formed from essentially additive-free BCDMH as described in Example 1. Tests comparing water content of dry particulate solids to the hardness or tablet crush strength as measured in pounds per square inch for unaged tablets, and tablets aged for twenty-four hours and forty-eight hours were performed as described in Example 2. The tablets were formed from particles substantially within the range of −10 to +20 sieve classification. The water content was measured by the standard Loss on Drying method. The following are results:

| Water Content | Tablet Crush Strength psi at Break | | |
|---|---|---|---|
| | 0 hr. | 24 hr. | 48 hr. |
| 0.67% | 19.8 | 19.7 | 24.3 |
| 1.01% | 23.4 | 23.3 | 36.6 |
| 1.31% | 31.5 | 37.5 | 62.0 |
| 1.65% | 37.9 | 32.0 | 44.5 |
| 2.02% | 34.7 | 45.8 | 64.1 |

Table 3 suggests that water concentrations approaching two percent in the BCDMH particulate improves tablet hardness. However, water concentrations greater than 1.5% causes product instability, discoloration and corrosion of tableting equipment. It should also be noted that although certain water concentrations have been found to affect the hardness of N-halohydantoin tablets, it is not commercially feasible to vary hardness by controlling water content. It is therefore suggested that the water concentrations of less than 1.5% are optimal.

EXAMPLE 4

Tablets of various sodium carbonate concentrations and about one percent water were formed from BCDMH as described in Example 1. Tests comparing the additive, i.e. sodium carbonate, concentration of the tablets and length of aging or curing to the tablet hardness or crush strength as measured in pounds per square inch were performed as described in Example 2. The tablets were formed from particles substantially within the range of −10 to +20 sieve classification. The following are the results:

| Concentration of Sodium Carbonate | Length of Aging Time psi at Break | | |
|---|---|---|---|
| | 0 hr. | 24 hr. | 48 hr. |
| 0% | 26.2 | 26.0 | 26.5 |
| 1% | 33.4 | 49.5 | 59.8 |
| 2% | 33.4 | 57.6 | 64.2 |
| 3% | 41.3 | 61.6 | 92.2 |

Table 4 indicates that tablet hardness is directly proportional to chemical additive concentration which is limited by the allowable minimum assay of the final product.

EXAMPLE 5

Tablets free of sodium carbonate and tablets containing two percent sodium carbonate, both tablet types containing about one percent water, were formed from BCDMH as described in Example 1. Brominator tests comparing dissolution rate of additive-free BCDMH tablets to that of BCDMH tablets containing two percent sodium carbonate were performed by filling a tube with solid BCDMH, injecting water from one end at a flow rate controlled by a valve and measuring the chlorine concentration in the effluent at the listed points in time after initiating water flow. The tablets were formed from particles substantially within the range of −10 to +20 sieve classification. The results follow:

| Time (hrs) | Additive-free Tablets | Two percent carbonate Tablets |
|---|---|---|
| 1 | 82.53 mg/l | 50.37 mg/l |
| 2 | 42.68 mg/l | 37.06 mg/l |
| 20 | 17.63 mg/l | 17.40 mg/l |
| 24 | 15.17 mg/l | 14.60 mg/l |
| 25 | 15.86 mg/l | 16.26 mg/l |
| 26 | 15.52 mg/l | 16.70 mg/l |
| 42 | 12.69 mg/l | 13.40 mg/l |
| 43 | 12.34 mg/l | 11.80 mg/l |
| 45 | 12.34 mg/l | 13.10 mg/l |
| 48 | 11.99 mg/l | 12.20 mg/l |

Table 5 indicates little difference in the dissolution rate of additive-free BCDMH tablets to that of BCDMH tablets containing two percent sodium carbonate. The only measurable differences occur early in the test period and are accounted for by sloughing of surface dust. The test discloses no change of dissolution rate by chemical additives when applied through a chemical feeder.

EXAMPLE 6

Tablets free of sodium carbonate and tablets containing one, two and three percent sodium carbonate, all tablet types containing about one percent water, were formed from BCDMH as described in Example 1. Tests comparing dissolution rate of additive-free BCDMH tablets to the concentration of sodium carbonate additive in the tablets were performed by filling a two liter beaker with deionized water and tablets of BCDMH, placing the beaker on a stirrer revolving at 100 rpm, taking samples at the following points of time after mixture of the tablets and water and measuring the chlorine concentration. The tablets were formed from particles substantially within the range of −10 to +20 sieve classification. The results follow:

| Time (hrs) | Additive-free | 1% | 2% | 3% |
|---|---|---|---|---|
| 0.5 | 38.84 mg/l | 50.74 mg/l | 53.25 mg/l | 87.07 mg/l |
| 1.0 | 93.34 mg/l | 82.69 mg/l | 95.22 mg/l | 126.54 mg/l |
| 1.5 | 131.55 mg/l | 119.65 mg/l | 133.43 mg/l | 159.74 mg/l |
| 3.0 | 219.25 mg/l | 253.07 mg/l | 231.15 mg/l | 248.06 mg/l |
| 4.0 | 286.27 mg/l | 293.16 mg/l | 289.40 mg/l | 288.15 mg/l |
| 5.0 | — | 338.58 mg/l | 339.52 mg/l | 357.06 mg/l |
| 6.0 | 409.68 mg/l | 388.38 mg/l | 391.51 mg/l | 400.59 mg/l |

Table 6 indicates little difference in the dissolution rate of additive-free BCDMH tablets to that of BCDMH tablets containing 1%, 2%, or 3% sodium carbonate additive under laboratory conditions.

EXAMPLE 7

Additive-free, dried BCDMH was compressed into 1⅛ inch diameter tablets of twenty grams each. The tablets were formed from particles substantially within the range of −10 to +20 sieve classification. Tablets of about one percent water and various densities, ranging from 1.5 to 1.8 gms/cm$^3$, were formed as described in Example 1 and the crush strengths measured as described in Example 2. The green crush strength of these tablets ranged from twenty-three to thirty-three psi, averaging 26.7 psi. Similar tablets cured by aging for twenty-four hours in sealed shipping containers had crush strengths that ranged from twenty to thirty-five psi, averaging 27.2 psi.

EXAMPLE 8

Dried BCDMH with 3.0% anhydrous sodium carbonate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from thirty-two to fifty-five psi, averaging 41.3 psi. Similar tablets cured by aging for twenty-four hours in sealed shipping containers had crush strengths that ranged from forty-five to ninety-two psi, averaging 61.6 psi.

EXAMPLE 9

Dried BCDMH with 3.0% sodium carbonate monohydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from thirty-nine to sixty-four psi, averaging 44.4 psi. Similar tablets cured by aging for twenty-four hours in sealed shipping containers had crush strengths that ranged from thirty-six to seventy-four psi, averaging 49.6 psi.

EXAMPLE 10

Dried BCDMH with 3.0% sodium carbonate decahydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from twenty-one to fifty-seven psi, averaging 38.8 psi. Similar tablets cured by aging for twenty-four hours in sealed shipping containers had crush strengths that ranged from forty-five to seventy-four psi, averaging 51.8 psi.

EXAMPLE 11

Dried BCDMH with 3.0% sodium percarbonate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from thirty-four to fifty-eight psi, averaging 43.8 psi. Similar tablets cured by aging for twenty-four hours in sealed shipping containers had crush strengths that ranged from forty-three to eighty-two psi, averaging 71.8 psi.

EXAMPLE 12

Dried BCDMH with 3.0% anhydrous sodium silicate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from forty to sixty-one psi, averaging 49.2 psi. Similar tablets cured by aging for twenty-four hours in sealed shipping containers had crush strengths that ranged from thirty-nine to one hundred ten psi, averaging 84.8 psi.

EXAMPLE 13

Dried BCDMH with 3.0% sodium meta-silicate nonohydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from forty-five to fifty-three psi, averaging 51.0 psi. Similar tablets cured by aging for twenty-four hours in sealed shipping containers had crush strengths that ranged from ninty to one-hundred-five psi, averaging 100 psi.

EXAMPLE 14

Dried BCDMH with 1.0% sodium meta-silicate nonohydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from twenty-two to forty-four psi, averaging 36.4 psi. Similar tablets cured by aging for twenty-four hours in sealed shipping containers had crush strengths that ranged from forty-seven to fifty-nine psi, averaging 56.0 psi.

EXAMPLE 15

Dried BCDMH with 3.0% sodium meta-silicate pentahydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from twenty-seven to thirty psi, averaging 29.3 psi. Similar tablets cured by aging for twenty-four hours in sealed shipping containers had crush strengths that ranged from fifty-four to one hundred psi, averaging 79.0 psi.

EXAMPLE 16

Dried BCDMH with 3.0% sodium borate decahydrate was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from thirty-five to forty-one psi, averaging 38.2 psi. Similar tablets cured by aging for twenty-four hours in sealed shipping containers had crush strengths that ranged from fifty-seven to eighty-five psi, averaging 66.8 psi.

EXAMPLE 17

Dried BCDMH with 3.0% magnesium oxide was compressed into 1⅛ inch diameter tablets of twenty grams each. The tablets were formed from particles substantially within the range of −10 to +20 sieve classification. The tablets of about one percent water and various densities, ranging from 1.5 to 1.8 gms/cm$^3$, were formed as described in Example 1 and the crush strengths measured as described in Example 2. The green crush strength of these tablets ranged from four to seventeen psi, averaging ten psi. Similar tablets cured by aging for twenty-four hours in sealed shipping containers had crush strengths that ranged from twenty-two to forty-nine psi, averaging 31.8 psi.

The results of Examples 7 through 15 are tabulated below:

| Example | Additive | Average Crush Green Strength (lbs.) (Unaged) | Strength (lbs.) Aged 24 Hrs. |
|---|---|---|---|
| 7 | None | 26.7 | 27.2 |
| 8 | 3% Anhydrous Sodium Carbonate | 41.3 | 61.6 |
| 9 | 3% Sodium Carbonate Monohydrate | 44.4 | 49.6 |
| 10 | 3% Sodium Carbonate Decahydrate | 38.8 | 51.8 |
| 11 | 3% Sodium Percarbonate | 43.8 | 71.8 |
| 12 | 3% Anhydrous Sodium Silicate | 49.2 | 84.8 |
| 13 | 3% Sodium Meta-Silicate Nonohydrate | 51.0 | 100.0 |
| 14 | 1% Anhydrous Meta-Silicate Nonohydrate | 36.4 | 56.0 |
| 15 | 3% Sodium Meta-Silicate Pentahydrate | 29.3 | 79.0 |
| 16 | 3% Sodium Borate Decahydrate | 38.2 | 66.8 |
| 17 | 3% Magnesium Oxide | 10.0 | 31.8 |

In view of the above, it will be seen that the several objects of the invention are achieved.

As various changes could be made in the above constructions without departing from the scope of the invention, it is intended that all matter contained in the above description shall be interpreted as illustrative and not in a limiting sense.

What is claimed is:

1. A process for the manufacture of densified N-halohydantoin compound of the formula

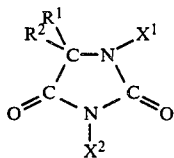

where R$^1$ and R$^2$ are independently selected from the group consisting of hydrogen and lower alkyl, and X$^1$ and X$^2$ are independently selected from the group consisting of bromine, chlorine and hydrogen, at least one of X$^1$ and X$^2$ being halogen, the process comprising blending dry, particulate N-halohydantoin compound with dry, particulate salt, said salt comprising a cation selected from the group consisting of lithium, sodium, potassium, magnesium and calcium and an anion selected from the group consisting of carbonate, bicarbonate, borate, silicate, phosphate, percarbonate, and perphosphate, to form a dry mixture and compacting the mixture.

2. A process as set forth in claim 1 wherein R$^1$ and R$^2$ each comprise methyl.

3. A process as set forth in claim 2 wherein X$^1$ comprises bromine and X$^2$ comprises chlorine.

4. A process as set forth in claim 3 wherein the particulate N-halohydantoin compound and the particulate salt comprise particles of size substantially within the range of −10 to +20 sieve classification.

5. A process as set forth in claim 3 wherein the salt is added in a proportion such that it constitutes between about one-half percent to about three percent by weight of the mixture.

6. A process as set forth in claim 3 further comprising the step of aging tablets formed by the densification of the mixture at ambient temperature for at least twenty-four hours.

7. A process as set forth in claim 3 wherein the salt comprises sodium carbonate.

8. A process as set forth in claim 3 wherein the salt comprises sodium silicate.

9. A process as set forth in claim 5 wherein the salt comprises sodium silicate.

10. A process as set forth in claim 3 wherein the salt comprises sodium percarbonate.

11. A process as set forth in claim 5 wherein the salt comprises sodium percarbonate.

12. A process as set forth in claim 3 wherein the salt comprises sodium borate.

13. A process as set forth in claim 5 wherein the salt comprises sodium borate.

14. A dry tablet produced by the process of claim 1, said tablet comprising N-halohydantoin compound and salt, said tablet having a green crush strength greater than about thirty-one pounds and a density of about 1.5 grams per cubic centimeter to about 1.8 grams per cubic centimeter.

15. A dry tablet produced by the process of claim 3, said tablet comprising N-halohydantoin compound and salt, said tablet having a green crush strength greater than about thirty-one pounds and a density of about 1.5 grams per cubic centimeter to about 1.8 grams per cubic centimeter.

16. A dry tablet produced by the process of claim 5, said tablet comprising N-halohydantoin compound and salt, said tablet having a green crush strength greater than about thirty-one pounds and a density of about 1.5 grams per cubic centimeter to about 1.8 grams per cubic centimeter.

17. A dry tablet produced by the process of claim 9, said tablet comprising N-halohydantoin compound and salt, said tablet having a green crush strength greater than about thirty-one pounds and a density of about 1.5 grams per cubic centimeter to about 1.8 grams per cubic centimeter.

18. A dry tablet comprising N-halohydantoin compound and between about one-half percent and about three percent by weight salt, and having a density of about 1.5 grams per cubic centimeter to about 1.8 grams per cubic centimeter.

19. A dry tablet comprising bromochlorodimethylhydantoin and between about one-half percent and about three percent by weight sodium carbonate, and having a density of about 1.5 grams per cubic centimeter to about 1.8 grams per cubic centimeter.

20. A dry tablet comprising bromochlorodimethylhydantoin and between about one-half percent and about three percent by weight sodium silicate, and having a density of about 1.5 grams per cubic centimeter to about 1.8 grams per cubic centimeter.

21. A dry tablet comprising bromodimethylhydantoin, chlorodimethylhydantoin and between about one-half percent and about three percent by weight sodium carbonate, and having a density of about 1.5 grams per cubic centimeter to about 1.8 grams per cubic centimeter.

22. A dry tablet comprising bromodimethylhydantoin, chlorodimethylhydantoin and between about one-half percent and about three percent by weight sodium silicate, and having a density of about 1.5 grams per cubic centimeter to about 1.8 grams per cubic centimeter.

23. A process for the manufacture of densified bromochlorodimethylhydantoin of the formula

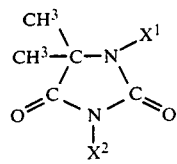

where $X^1$ and $X^2$ are selected from the group consisting of bromine and chlorine, the process comprising blending dry, particulate bromochlorodimethylhydantoin with dry, particulate sodium carbonate to form a dry mixture and compacting the mixture, whereby the resulting tablets contain between about one-half percent and about three percent sodium carbonate.

24. A process for the manufacture of tablets of bromochlorodimethylhydantoin of the formula

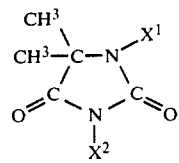

where $X^1$ and $X^2$ are selected from the group consisting of bromine and chlorine, the process comprising blending dry, particulate bromochlorodimethylhydantoin with dry, particulate sodium silicate to form a dry mixture and compacting the mixture, whereby the resulting tablets contain between about one-half percent and about three percent sodium silicate.

25. A dry mixture comprising dry, particulate N-halohydantoin compound and dry, particulate salt, said salt comprising a cation selected from the group consisting of sodium, potassium, magnesium and zinc and an anion selected from the group consisting of carbonate, bicarbonate, borate, silicate, phosphate, percarbonate, and perphosphate, the mixture comprising particles of size substantially within the range of $-10$ to $+20$ sieve classification.

* * * * *